United States Patent
Luo

(10) Patent No.: US 9,546,864 B2
(45) Date of Patent: Jan. 17, 2017

(54) ALIGNMENT INSPECTING SYSTEM FOR LIQUID CRYSTAL SUBSTRATE

(71) Applicant: Shenzhen China Star Optoelectronics Technology Co., Ltd., Shenzhen, Guangdong (CN)

(72) Inventor: Ping Luo, Guangdong (CN)

(73) Assignees: Shenzhen China Star Optoelectronics Technology Co., Ltd, Shenzhen, Guangdong (CN); Optoelectronics Technology Co., Ltd, Guangdong (CN)

( * ) Notice: Subject to any disclaimer, the term of this patent is extended or adjusted under 35 U.S.C. 154(b) by 478 days.

(21) Appl. No.: 14/239,116

(22) PCT Filed: Jan. 14, 2014

(86) PCT No.: PCT/CN2014/070612
§ 371 (c)(1),
(2) Date: Feb. 14, 2014

(87) PCT Pub. No.: WO2015/100802
PCT Pub. Date: Jul. 9, 2015

(65) Prior Publication Data
US 2015/0323314 A1    Nov. 12, 2015

(30) Foreign Application Priority Data

Dec. 31, 2013 (CN) .......................... 2013 1 0753086

(51) Int. Cl.
*B25B 9/00* (2006.01)
*G01B 11/27* (2006.01)
(Continued)

(52) U.S. Cl.
CPC ............... *G01B 11/27* (2013.01); *G01N 1/286* (2013.01); *G02F 1/1303* (2013.01); *G02F 1/1333* (2013.01); *G02F 2001/133354* (2013.01)

(58) Field of Classification Search
CPC .... G02F 1/1303; G02F 1/1333; G02F 1/1393; G02F 1/13; G02F 1/141; G02F 1/1337; B25B 5/006; B25B 5/003; B25B 5/06; B25B 5/163; B25B 5/105; B25B 5/142; B25B 5/08
See application file for complete search history.

(56) References Cited

U.S. PATENT DOCUMENTS 5,031,547 A * 7/1991 Hirose ................. B23Q 1/4866
108/137
5,501,436 A * 3/1996 Miller ................. H05K 13/0069
269/254 CS
(Continued)

FOREIGN PATENT DOCUMENTS

CN        201569821 U    9/2010

*Primary Examiner* — Lee D Wilson
(74) *Attorney, Agent, or Firm* — Andrew C. Cheng

(57) ABSTRACT

The present invention relates to an alignment inspecting system for liquid crystal substrate, comprises an alignment mechanism located on corners of the substrate, and the alignment mechanism including a horizontal alignment device for exerting pressure to edges of the substrate, wherein a flattening device for applying longitudinal pressure to the substrate is further included. The present invention can be concluded with the following advantages: this alignment inspecting system for liquid crystal substrate can be used to correct the bending of the substrate during alignment process, so as to reduce the bending and deformation of the substrate which in turn creates poor contact between the probe and the substrate. As a result, incorrect reading can be avoided.

7 Claims, 2 Drawing Sheets

(51) Int. Cl.
*G01N 1/28* (2006.01)
*G02F 1/13* (2006.01)
*G02F 1/1333* (2006.01)

(56) References Cited

U.S. PATENT DOCUMENTS

| | | | | |
|---|---|---|---|---|
| 6,262,582 B1 * | 7/2001 | Barringer | ........... | G01R 31/2887 269/254 CS |
| 6,328,296 B2 * | 12/2001 | Tyveleijn | ................ | B25B 11/02 269/287 |
| 7,971,863 B2 * | 7/2011 | Chen | ......................... | B25B 5/06 269/289 R |
| 2015/0323314 A1 * | 11/2015 | Luo | ........................ | G01B 11/27 356/244 |

* cited by examiner

ALIGNMENT INSPECTING SYSTEM FOR LIQUID CRYSTAL SUBSTRATE

FIELD OF THE INVENTION

The present invention relates to a manufacturing process of liquid crystal display panel, and more particularly, to an aligning system of liquid crystal substrate alignment inspecting apparatus after HVA (high resolution vertical alignment) alignment.

BACKGROUND OF THE INVENTION

In the manufacturing process of liquid crystal display panel, after HVA (high resolution vertical alignment) alignment, the liquid crystal substrate is checked by the liquid crystal inspecting apparatus with a nominated voltage is applied to the substrate, the substrate is lit and an image is captured by the CCD (charge coupled device), then the captured image is compared with the internal pre-established image so as to determine whether the alignment is qualified or not. For a substrate with a dimension up to 2200 mm*2500 mm, feeding it into the inspecting apparatus will easily cause it to bend and deform during the alignment checking process. When the voltage supplier is moved upward, it may readily create poor electrical contact between the probe and the substrate, resulting the image captured by the CCD (charge coupled device) is inconsistent with the actual situation. An inaccurate determination could be resulted.

SUMMARY OF THE INVENTION

The object of the present invention is to make a modification to the existing aligning system for providing an alignment inspecting apparatus for liquid crystal substrate so as to overcome the above technical issues.

In order to achieve the purposes of the present invention, the alignment inspecting system for liquid crystal substrate comprises an alignment mechanism located on corners of the substrate, and the alignment mechanism includes a horizontal alignment device for exerting pressure to edges of the substrate, wherein a flattening device for applying longitudinal pressure to the substrate is further included.

Wherein the alignment mechanism includes a horizontal alignment wheel, an alignment cylinder connected to the horizontal alignment device, and a first control device for controlling the alignment cylinder; wherein the horizontal alignment device further includes a working platform; and wherein the alignment cylinder is coupled to the working platform.

Wherein the first control device is a solenoid valve.

Wherein the flattening device includes a pressure wheel for operation exerted on the substrate, a pressure wheel cylinder connected to the pressure wheel, and a second control device for controlling the pressure wheel cylinder.

Wherein the second control device is a solenoid valve.

Wherein the pressure wheel cylinder of the flattening device is connected to the working platform.

Wherein the connection of the pressure wheel and the pressure wheel cylinder is that: the pressure wheel is fixed on an operational arm by a pin shaft, the operational arm is coupled to the pressure wheel cylinder by a linkage; and the operational arm is defined with a keyway in which a key from the pressure wheel is inserted therein.

Wherein the connection of the pressure wheel and the pressure wheel cylinder is that: the pressure wheel is fixed on an operational arm by a pin shaft, the operational arm is coupled to the pressure wheel cylinder by its own weight, the operational arm cylinder is controlled by a third control device.

Wherein each of the four corners of the substrate is associated with the flattening device.

The present invention can be concluded with the following advantages: this alignment inspecting system for liquid crystal substrate can be used to correct the bending of the substrate during alignment process, so as to reduce the bending and deformation of the substrate which in turn creates poor contact between the probe and the substrate. As a result, incorrect reading can be avoided.

DETAILED DESCRIPTION OF PREFERRED EMBODIMENTS

The present invention will be further described along with the accompanied drawings.

Figure 1:
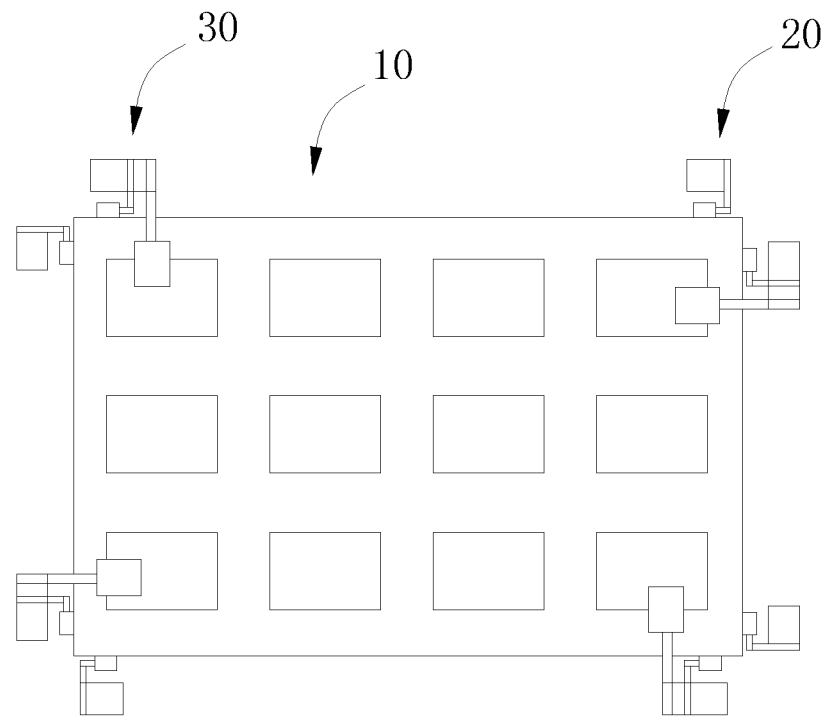
FIG. 1 is a top view of an alignment inspecting system for liquid crystal substrate alignment.
Figure 2:
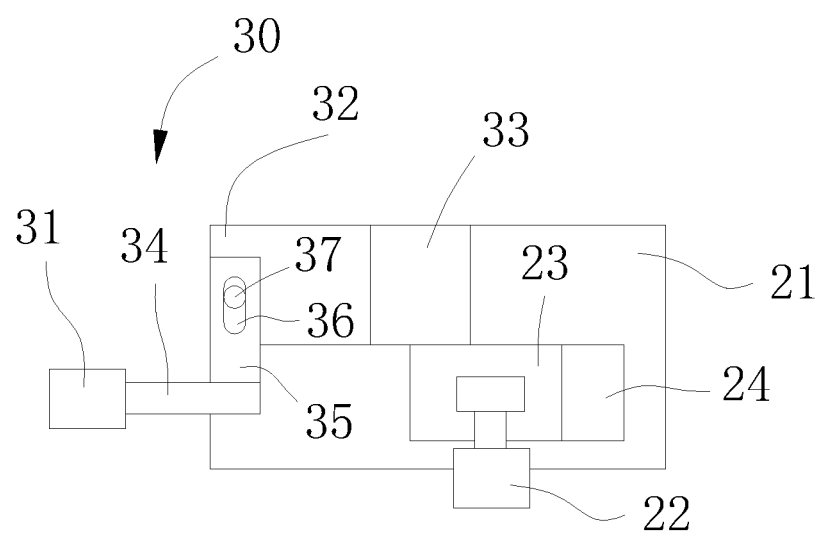
FIG. 2 is an illustrational view of an aligning system of alignment inspecting apparatus for liquid crystal display in accordance with an embodiment of the present invention.

Referring to FIGS. 1 and 2, the alignment inspecting system for liquid crystal substrate comprises a plurality of alignment mechanisms located at the four corners of the large-scale substrate 10. Wherein the alignment mechanism is configured by horizontal alignment device 20 and flattening device 30. The horizontal alignment device 20 is configured by a working platform 21, a horizontal alignment wheel 22 and an alignment cylinder 23 that connected to the horizontal alignment wheel 22 and a first control device 24 for controlling the alignment cylinder; wherein the alignment cylinder 23 is coupled to the working platform 21. The first control device 24 is a solenoid valve. The position adjustment for substrate 10 facilitated by horizontal alignment wheel 22 located on the edge corners. When the substrate 10 is bent, the flatting device 30 applies longitudinal pressure to the substrate 10 for flattening the substrate 10.

The flattening device 30 includes a pressure wheel 31 for operation exerted on the substrate 10, a pressure wheel cylinder 32 that is coupled with pressure wheel 31 and a second control device 33 for controlling the pressure wheel cylinder 32; wherein the second control device 33 is a solenoid valve, and is installed in the control panel of working platform 21. Both ends of the solenoid are arranged with hoses coupled to inlets of the pressure wheel cylinder 32. The working platform 21 commends the solenoid valve to open and close by the PLC (programmable logic controller). When the solenoid valve 33 is opened, the pressure wheel cylinder 32 will push the pressure wheel 31 to proceed to the top of the substrate 10, and when the solenoid valve 33 is closed, the pressure wheel cylinder 32 will pull the pressure wheel 31 back to its original position to avoid interference with pressure wheel 31 when the substrate 10 is moving out. The pressure wheel cylinder 32 of the flattening device 30 is connected with working platform 21. The pressure wheel 31 is fixed on an operational arm 35 by a pin shaft 34, the operational arm 35 is coupled to the pressure wheel cylinder 32 by its own weight. In the present embodiment, the operational arm 35 is defined with a keyway 36 and there is a positioning pillar 37 for through the keyway 36 on the pressure wheel cylinder 32.

With a further and detailed description of the operational procedures, the present invention can be better understood.

When the substrate 10 is fed from inlet to the operating room, eight sets of alignment mechanism placed in the four corners of the substrate 10 are going to conduct alignment process to sides of the substrate 10, wherein one of two alignment mechanisms located at each corner has modified into the configuration as described above, i.e., the flattening device 30. During alignment process, the substrate 10 tends to deform due to its overlarge dimension and size, in this moment, the flatting device 30 will exert a longitudinal pressure to the substrate 10 and flattens the substrate 10. As it can be readily seen from figures, the flattening device 30 of this application is upgraded with a pressure wheel cylinder 32 and the solenoid valve i.e. the second control device 33 to displace the pressure wheel 31 horizontally to achieve the desired position. The pressure wheel 31 is fixed on the operational arm 35 by a pin shaft 34, and the operational arm 35 is coupled to the pressure wheel cylinder 32 by its own weight. The pressure wheel 31 is located at the lowest position due to its own weight. When the pressure wheel 31 is driven by the pressure wheel cylinder 32 horizontally to reach to substrate 10, the pressure wheel 31 will contact with the edge of the substrate 10 firstly. With the continued displacement of the pressure wheel 31, it will further moves inwardly on substrate 10, and the pressure wheel 31 will be lifted slowly by the edges of substrate 10 sitting the substrate 10 with its own weight. If the substrate 10 is bent, the substrate 10 will be flattened by the force exerted thereon by the pressure wheel 31. The coupling between the operational arm 35 and the pressure wheel cylinder 32 is moveable or pivotal, i.e. the keyway 36 is moving up and down relatively to the stationary positioning pillar 37.

Figure 3:
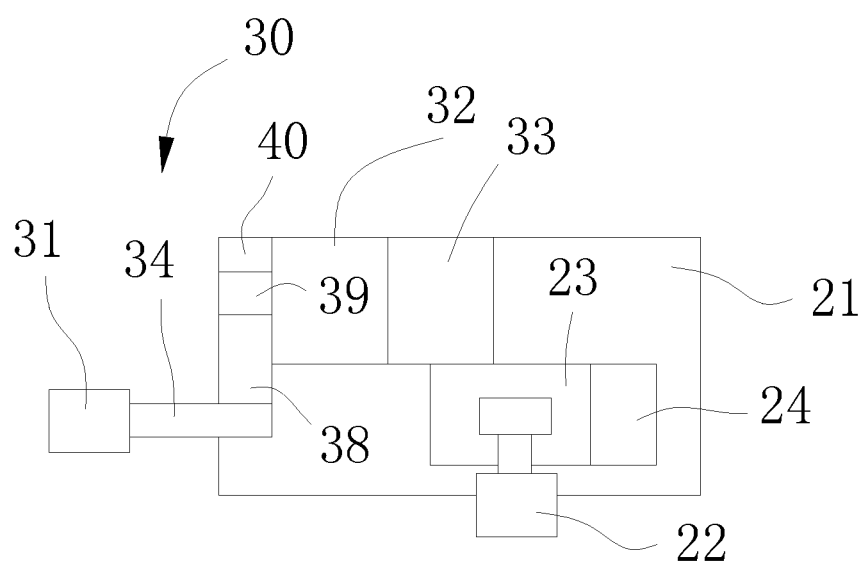
FIG. 3 is an illustrational view of an aligning system of alignment inspecting apparatus for liquid crystal display in accordance with another embodiment of the present invention.

In a further embodiment, as shown in FIG. 3, the intercoupling between the pressure wheel 31 and the pressure wheel cylinder 32 can be designed as: the pressure wheel 31 is fixedly mounted on an operational arm 38 by a pin shaft 34, and the operational arm 38 is coupled to the pressure wheel cylinder 32 by an operational arm cylinder 39.

Although embodiments of the present invention have been described, persons of the skilled in the art should understand that any modification of equivalent structure or equivalent process without departing from the spirit and scope of the present invention limited by the claims is allowed.

The invention claimed is:

1. An alignment inspecting system for liquid crystal substrate, comprising an alignment mechanism located on corners of the substrate, and the alignment mechanism including a horizontal alignment device for exerting pressure to edges of the substrate,
    wherein a flattening device for applying longitudinal pressure to the substrate is further included;
    wherein the horizontal alignment device includes a horizontal alignment wheel, an alignment cylinder connected to the horizontal alignment device, and a first control device for controlling the alignment cylinder;
    wherein the horizontal alignment device further includes a working platform; and wherein the alignment cylinder is coupled to the working platform;
    wherein the first control device is a solenoid valve.

2. An alignment inspecting system for liquid crystal substrate, comprising an alignment mechanism located on corners of the substrate, and the alignment mechanism including a horizontal alignment device for exerting pressure to edges of the substrate, wherein a flattening device for applying longitudinal pressure to the substrate is further included;
    wherein the horizontal alignment device includes a horizontal alignment wheel, an alignment cylinder connected to the horizontal alignment device, and a first control device for controlling the alignment cylinder;
    wherein the horizontal alignment device further includes a working platform; and wherein the alignment cylinder is coupled to the working platform;
    wherein the flattening device includes a pressure wheel for operation exerted on the substrate, a pressure wheel cylinder connected to the pressure wheel, and a second control device for controlling the pressure wheel cylinder;
    wherein the second control device is a solenoid valve.

3. The alignment inspecting system for liquid crystal substrate as recited in claim 1, wherein the connection of the pressure wheel and the pressure wheel cylinder is that: the pressure wheel is fixed on an operational arm by a pin shaft; the operational arm is coupled to the pressure wheel cylinder by a linkage; and the operational arm cylinder is controlled by a third control device.

4. The alignment inspecting system for liquid crystal substrate as recited in claim 2, wherein the connection of the pressure wheel and the pressure wheel cylinder is that: the pressure wheel is fixed on an operational arm by a pin shaft; the operational arm is coupled to the pressure wheel cylinder by a linkage; and the operational arm cylinder is controlled by a third control device.

5. The alignment inspecting system for liquid crystal substrate as recited in claim 1, wherein the connection of the pressure wheel and the pressure wheel cylinder is that: the pressure wheel is fixed on an operational arm by a pin shaft; and the operational arm is coupled to the pressure wheel cylinder by weight of the operational arm.

6. The alignment inspecting system for liquid crystal substrate as recited in claim 2, wherein the connection of the pressure wheel and the pressure wheel cylinder is that: the pressure wheel is fixed on an operational arm by a pin shaft; and the operational arm is coupled to the pressure wheel cylinder by weight of the operational arm.

7. The alignment inspecting system for liquid crystal substrate as recited in claim 3, wherein the operational arm is defined with a keyway in which a key from the pressure wheel is inserted therein.

* * * * *